(12) United States Patent
Yang et al.

(10) Patent No.: US 8,173,444 B2
(45) Date of Patent: May 8, 2012

(54) METAL PARTICLE AND A TESTING METHOD USING THE SAME

(75) Inventors: Bo Yang, Kanagawa (JP); Hiroyuki Chiku, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 354 days.

(21) Appl. No.: 12/369,433

(22) Filed: Feb. 11, 2009

(65) Prior Publication Data
US 2009/0203153 A1 Aug. 13, 2009

(30) Foreign Application Priority Data

Feb. 12, 2008 (JP) ................................. 2008-029983

(51) Int. Cl.
*G01N 33/553* (2006.01)
(52) U.S. Cl. ......... 436/525; 422/425; 428/402; 428/403
(52) U.S. Cl. ..............................................................
(58) Field of Classification Search .................. 422/425; 428/402, 403; 436/525
See application file for complete search history.

(56) References Cited

U.S. PATENT DOCUMENTS

| | | | | |
|---|---|---|---|---|
| 4,272,506 A | * | 6/1981 | Schwarzberg | ................ 436/512 |
| 5,710,049 A | * | 1/1998 | Noppe et al. | .................. 436/525 |
| 2004/0202720 A1 | * | 10/2004 | Wightman et al. | ........... 424/489 |
| 2009/0047746 A1 | | 2/2009 | Tamiya et al. | |

FOREIGN PATENT DOCUMENTS

| | | | |
|---|---|---|---|
| JP | 2004-233127 A | | 8/2004 |
| JP | 2006-177914 | * | 8/2004 |
| JP | 2006-177914 A | | 7/2006 |
| JP | 2006-266743 A | | 10/2006 |
| WO | WO 2007/061098 A1 | | 5/2007 |

OTHER PUBLICATIONS

Japanese Office Action with the English translation dated Aug. 23, 2011, for Application No. 2008-029983.

* cited by examiner

*Primary Examiner* — Bao Thuy L Nguyen
(74) *Attorney, Agent, or Firm* — Birch, Stewart, Kolasch & Birch, LLP

(57) ABSTRACT

An object of the present invention is to provide a metal particle with which a highly-sensitive testing method can be conducted, and a testing method using such metal particle. The present invention provides a metal particle, which is produced by coating a metal particle labeled with a molecule binding to an analyte with a mixture of two or more types of water-soluble polymer having a mercapto group, a dithiol group or a sulfide group and differing in molecular weight.

11 Claims, 1 Drawing Sheet

METAL PARTICLE AND A TESTING METHOD USING THE SAME

TECHNICAL FIELD

The present invention relates to a metal particle and a testing method using the same, and particularly an immunochromatographic testing method.

BACKGROUND ART

Many substances that act in trace amounts cannot be detected by conventional detection methods based on immunochromatographic methods. Recently, the development of rapid, convenient, and highly sensitive methods for detecting such substances has become essential. An immunochromatographic method with higher sensitivity than conventionally known immunochromatographic methods is required. Hence, various amplification techniques have been developed.

For example, a method that has been proposed over years involves directly or indirectly labeling aggregates formed of a specific binder and a binding substance with a tiny metal particles and particularly, with gold particles, so as to detect the aggregates. Metal particles possess advantages in that they allow direct visual inspection and signals to be generated are permanent and do not rapidly deteriorate. Hence, such metal particles have generated interest as labeling substances for simple and rapid tests. Furthermore, metal labels, and preferably, gold labels, have extremely low hygiene risks associated with operations that use them, so that they are more preferable than radioisotope labels. A general method involves labeling an antibody with a colloidal gold label and then blocking with a protein and a polymer the non-labeled portions to which no antibodies have adhered. Currently, a colloidal gold label amplification technique has been disclosed that uses a water-soluble polymer (acetal-PEG-SH, molecular weight of 10000) having a functional group capable of binding to metal particle surfaces and a reaction group capable of covalently binding to antibodies at the same time (JP Patent Publication (Kokai) No. 2005-214907 A). Moreover, a technique has been reported by which nonspecific adsorption of protein is suppressed by forming a polymer brush layer on the surface of gold using mercapto polyethylene glycols (HS-PEGs) with different molecular weights in a surface Plasmon (SPR) sensor (Katsumi Uchida. et al. Anal. Chem. 2005, 77, 1075-1080). However, it has never been reported that in an immunochromatographic method a metal particle label had been labeled with an antibody and then HS-PEGs having different molecular weights were used to improve detection sensitivity.

DISCLOSURE OF THE INVENTION

An object to be achieved by the present invention is to provide a metal particle with which a highly-sensitive testing method can be conducted, and a testing method using such metal particle.

As a result of intensive studies to achieve the above object, the present inventors have discovered that the sensitivity of testing method can be improved by coating the metal particle with a mixture of two or more types of water-soluble polymer having a mercapto group, a dithiol group, or a sulfide group and differing in molecular weight, in a testing method which comprises developing a complex formed of an analyte and a metal particle labeled with a molecule binding to the analyte on an insoluble carrier, and then capturing the complex of the analyte and the metal particle at a reaction site on the insoluble carrier that has a second molecule binding to the analyte, so as to detect the analyte. Thus, the present inventors have completed the present invention.

The present invention provides a metal particle, which is produced by coating a metal particle labeled with a molecule binding to an analyte with a mixture of two or more types of water-soluble polymer having a mercapto group, a dithiol group or a sulfide group and differing in molecular weight.

Preferably, each content of the two or more types of water-soluble polymer ranges from 0.001% by weight to 99.999% by weight.

Preferably, the water-soluble polymers are polyalkylene oxide polymers.

Preferably, the water-soluble polymers are polyethylene glycols.

Preferably, the metal particle is a gold colloidal particle.

The present invention further provides an immunochromatographic kit, which comprises at least (a) the metal particle of the present invention as mentioned above, (b) a reagent for a sensitization reaction, and (c) a porous carrier.

The present invention further provides a testing method, which comprises developing a complex formed of an analyte and the metal particle of the present invention as mentioned above on an insoluble carrier and capturing the complex of the analyte and the metal particle at a reaction site on the insoluble carrier that has a second molecule binding to the analyte, so as to detect the analyte.

Preferably, amplification is carried out using silver or a silver compound.

By the use of the metal particle of the present invention, immunochromatographic measurement can be carried out with high sensitivity.

Figure 1:
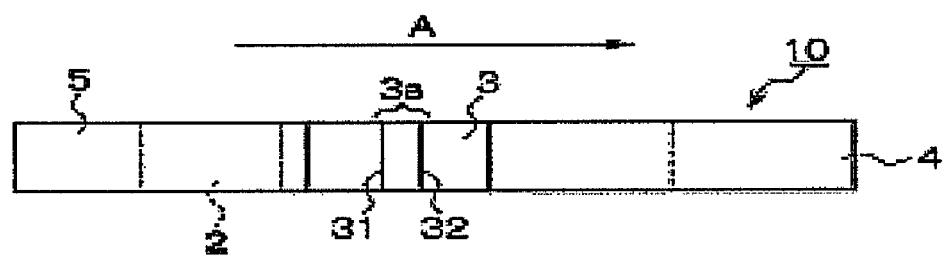
FIG. 1 is a plan view which schematically illustrates an embodiment of the immunochromatographic kit.

| | |
|---|---|
| 1: | Back adhesive sheet |
| 2: | Gold colloid antibody-retaining pad |
| 3: | Antibody-immobilized membrane |
| 3a: | Capturing site |
| 31: | Detection portion |
| 32: | Control portion |
| 4: | Absorbent pad |
| 5: | Sample-adding pad |
| 10: | Immunochromatographic kit |

BEST MODE FOR CARRYING OUT THE INVENTION

The metal particle of the present invention is preferably used in an immunochromatography kit.

1. Immunochromatography

In general, immunochromatography is a method for determining and/or measuring an analyte, simply, rapidly and specifically, by the following means. That is to say, a chromatographic carrier having at least one reaction zone comprising an immobilizing reagent (an antibody, an antigen, etc.) capable of binding to an analyte is used as an immobilization phase. On this chromatographic carrier, a dispersed liquid formed by dispersion of a labeling substance used in detection, which is modified by a reagent capable of binding to an analytical target, is used as a mobile phase, and the mobile phase is moved in the chromatographic carrier in a chromatographic manner. At the same time, the aforementioned analytical target specifically binds to the labeling substance used in detection, and they reach the aforementioned reaction zone. At the aforementioned reaction zone, a complex of the aforementioned analytical target and the aforementioned labeling substance used in detection specifically binds to the aforementioned immobilizing reagent. Utilizing the phenomenon whereby the labeling substance used in detection is concentrated in the immobilizing reagent portion only when the analytical target exists in an analyzed solution, the presence of a product to be detected in the analyzed solution is qualitatively and quantitatively analyzed by visual observation or using an adequate apparatus.

The immunochromatography kit in the present invention may comprise a compound containing silver and a reducing agent for silver ion. A signal is amplified by an amplification reaction using, as a core, a complex of the aforementioned analytical target and the aforementioned labeling substance used in detection binding to the aforementioned immobilizing reagent, so as to achieve high sensitivity. According to the present invention, a rapid and highly sensitive immunochromatography can be carried out.

2. Test Sample

The type of a test sample that can be analyzed by the immunochromatography of the present invention is not particularly limited, as long as it may comprise an analytical target. Examples of such a test sample include biological samples such as the body fluids of animals (particularly, a human) (e.g. blood, serum, plasma, spinal fluid, lacrimal fluid, sweat, urine, pus, runny nose, and sputum), excrements (e.g. feces), organs, tissues, mucous membranes, skin, a swab and a rinsed solution that are considered to contain them, and animals or plants themselves or the dried products thereof.

3. Pre-Treatment of Test Sample

In the immunochromatography of the present invention, the aforementioned test sample can directly be used. Otherwise, the aforementioned test sample can also be used in the form of an extract obtained by extracting it with a suitable extraction solvent, or in the form of a diluted solution obtained by diluting the aforementioned extract using a suitable diluent, or in the form of a concentrate obtained by concentrating the aforementioned extract by a suitable method. As the aforementioned extraction solvent, solvents used in common immunological analysis methods (e.g. water, a normal saline solution, a buffer, etc.) or water-miscible organic solvents that enable a direct antigen-antibody reaction as a result of dilution with the aforementioned solvents can be used.

4. Structure

Figure 2:
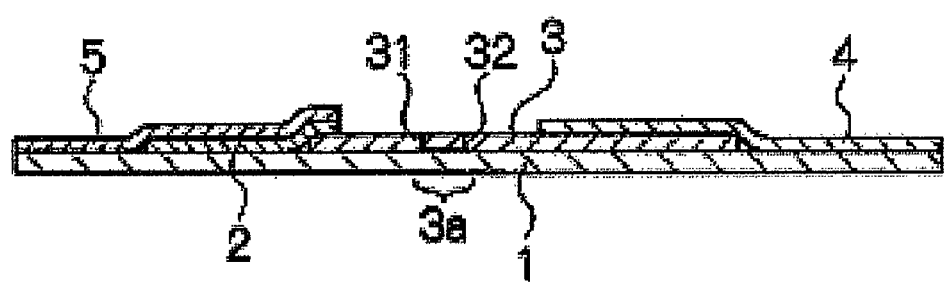
FIG. 2 is a longitudinal cross-sectional view which schematically illustrates a longitudinal cross-section of the immunochromatographic kit shown in FIG. 1.

The type of an immunochromatographic strip that can be used in the immunochromatography of the present invention is not particularly limited, as long as it is an immunochromatographic strip that can be used in a common immunochromatography. For example, FIG. 1 schematically shows a plane view of the conventional immunochromatographic strip, for example. FIG. 2 is a longitudinal sectional view schematically showing a longitudinal section of the immunochromatographic kit as shown in FIG. 1.

In an immunochromatographic strip 10 of the present invention, a sample-adding pad 5, a labeling substance-retaining pad (e.g. a gold colloid antibody-retaining pad) 2, a chromatographic carrier (e.g. an antibody-immobilized membrane) 3, and an absorbent pad 4 are disposed in this order on an adhesive sheet 5 from the upstream to the downstream of a development direction (a direction indicated with the arrow A in FIG. 1).

The chromatographic carrier 3 has a capturing site 3a and a detection zone (which is also referred to as a "detection portion") 31 that is a region on which an antibody or an antigen specifically binding to an analytical target is immobilized. The chromatographic carrier 3 also has a control zone (which is also referred to as a "control portion") 32 that is a region on which a control antibody or antigen is immobilized, as desired. Further, the detection zone 31 and the control zone 32 comprise organic silver salts used for amplification and reducing agents used for silver ion.

The labeling substance-retaining pad 2 can be produced by preparing a suspension containing a labeling substance, applying the suspension to a suitable absorbent pad (e.g. a glass fiber pad), and then drying it.

As the sample-adding pad 1, a glass fiber pad can be used, for example.

4-1. Labeling of Metal Particle for Detection

As a labeling of metal particle for detection, metals such as a metal colloid can be used. Examples thereof include a gold colloid, a silver colloid, a platinum colloid, an iron colloid, an aluminum hydroxide colloid, and a complex colloid thereof. Preferred examples include a gold colloid, a silver colloid, a platinum colloid, and a complex colloid thereof. A gold colloid and a silver colloid are particularly preferable in that the gold colloid exhibits a red color and the silver colloid exhibits a yellow color when they have an appropriate particle diameter. The mean particle diameter of a metal colloid is preferably between approximately 1 nm and 500 nm, more preferably between 1 nm and 50 nm, and particularly preferably between 1 nm and 15 nm. Such a metal colloid can be bound to a specifically binding substance according to conventionally known methods (e.g. The Journal of Histochemistry and Cytochemistry, Vol. 30, No. 7, pp. 691-696 (1982)). That is to say, a metal colloid is mixed with a specifically binding substance (e.g. an antibody) in a suitable buffer at room temperature for 5 or more minutes. After completion of the reaction, a precipitate obtained by centrifugation is dispersed in a solution containing a dispersant such as polyethylene glycol to obtain a metal colloid-labeled specifically binding substance of interest. When gold colloid particles are used as the metal colloid, commercially available gold colloid particles may be used. Alternatively, such gold colloid particles may be prepared by a common method, for example, by a method of reducing chlorauric acid with sodium citrate (Nature Phys. Sci., vol. 241, 20 (1973), etc.).

According to the present invention, in an immunochromatography using, as a labeling substance used in detection, a metal colloid labeling substance, a metallic sulfide labeling substance, a metal alloy labeling substance (hereinafter also referred to as a metallic labeling substance), or a metal-containing polymer particle labeling substance, the signal from the aforementioned metallic labeling substance can be amplified. Specifically, after formation of a complex of the analytical target and the labeling substance used in detection, silver ions supplied from a compound containing silver such as an organic silver salt are allowed to come into contact with a reducing agent for silver ions, so that the silver ions are reduced with the reducing agent to form silver particles. Thus, the silver particles are deposited on the aforementioned metallic labeling substance as a core, so that the metallic labeling substance is amplified to enable the high-sensitivity analysis of the analytical target. Accordingly, the conventionally known immunochromatography can directly be applied to the immunochromatography of the present invention with the exception that a reaction of precipitating silver particles generated as a result of reduction of silver ions with the reducing agent on the labeling substance of an immune complex is carried out, so as to analyze the thus amplified signal.

In the immunochromatography of the present invention, a metal colloid labeling substance or a metallic sulfide labeling substance may be used as a labeling substance for labeling an antibody or antigen which specifically binds to an analytical target (an antigen or an antibody), or for labeling a standard compound. The type of such a metal colloid labeling substance or a metallic sulfide labeling substance is not particularly limited, as long as it can be used in an ordinary immunochromatography. Examples of such a metal colloid labeling substance include a platinum colloid, a gold colloid, a palladium colloid, a silver colloid, and a mixture thereof. Examples of such a metallic sulfide labeling substance include sulfides of iron, silver, palladium, lead, copper, cadmium, bismuth, antimony, tin, and mercury. In the immunochromatography of the present invention, one or more selected from these metal colloid labeling substances and/or metallic sulfide labeling substances may be used as a labeling substance(s).

4-2 Molecule Binding to an Analyte

The term "molecule binding to an analyte" used regarding the immunochromatographic method of the present invention refers to a set of binding molecule having specificity for a subject to be analyzed. Examples of such a set of molecules include antigen-antibody, sugar-lectin, substrate-enzyme, hormone-receptor, and nucleic acid-complementary strand thereof. Antibodies are not particularly limited. For example, antiserum prepared from the serum of an animal immunized with a subject to be analyzed, an immunoglobulin fraction purified from antiserum, and a monoclonal antibody obtained by cell fusion using spleen cells of an animal immunized with a subject to be analyzed, or fragments of any thereof [e.g., $F(ab')_2$, Fab, Fab', or Fv] can be used.

4-3 Blocking Agent

A fine metal particle coated with a molecule binding to an analyte needs to be blocked with a blocking agent. In the present invention, as a blocking agent for a labeling of metal colloid, a mixture of two or more types of water-soluble polymer having a mercapto group, a dithiol group, or a sulfide group and differing in molecular weight is used.

Typical examples of a compound used as such a water-soluble polymer are as listed below, but the examples are not limited thereto. Water-soluble polymers such as polyethylene glycol, polyacrylic acid, polymethacrylate, polyvinylpyrrolidone, polyallylamine, dextran, polyacrylamide, polymethacrylamide, polyvinylphenol, polyvinyl benzoate, and polyvinyl alcohol are preferable. In particular, polyethylene glycol is preferable. Of two or more types of water-soluble polymer, the molecular weight of a water-soluble polymer with the higher molecular weight preferably ranges from 5,000 to 100,000. The molecular weight of the other water-soluble polymer, which is lower, preferably ranges from 1,000 to 5,000.

The method for using a water-soluble polymer having a mercapto group, a dithiol group or a sulfide group as a functional group capable of binding to metal particle surfaces is not particularly limited. Two or more types of water-soluble polymer may be used alternately or may be mixed simultaneously and then used.

Each content "r" of two or more types of water-soluble polymer is as defined below. In an example in which three types of blocking agent are used, r=a/(a+b+c) is employed, wherein a, b, and c are water-soluble polymers (e.g., mercaptopolyethylene glycols, HS-PEGs) differing in molecular weight and having functional groups capable of binding to metal particle surfaces. The content "r" of the above blocking agent preferably ranges from 0.001% by weight to 99.999% by weight.

4-4. Chromatographic Carrier

The chromatographic carrier is preferably a porous carrier. It is particularly preferably a nitrocellulose membrane, a cellulose membrane, an acetyl cellulose membrane, a polysulfone membrane, a polyether sulfone membrane, a nylon membrane, glass fibers, a nonwoven fabric, a cloth, threads or the like.

Usually, a substance used in detection is immobilized on a part of the chromatographic carrier to form a detection zone. The substance used in detection may be directly immobilized on a part of the chromatographic carrier via a physical or chemical bond. Alternatively, the substance used in detection may be bound physically or chemically to fine particles such as latex particles, and thereafter, the fine particles are immobilized on a part of the chromatographic carrier by trapping them thereon. After immobilization of the substance used in detection on the chromatographic carrier, the chromatographic carrier may preferably be subjected to a treatment for preventing unspecific adsorption, such as a treatment using an inert protein, and it may be then used.

4-5. Sample-Adding Pad

Examples of a material for the sample-adding pad include, but are not limited to, those having uniform characteristics, such as a cellulose filter paper, glass fibers, polyurethane, polyacetate, cellulose acetate, nylon, and a cotton cloth. A sample-adding portion not only acts to receive a sample containing the added analytical target, but also acts to filter off insoluble particles, etc. contained in the sample. Moreover, in order to prevent a decrease in analysis precision occurring during the analysis due to unspecific adsorption of the analytical target contained in the sample on the material of the sample-adding portion, the material constituting the sample-adding portion may be subjected to a treatment for preventing nonspecific adsorption before use.

4-6. Labeling Substance-Retaining Pad

Examples of a material for the labeling substance-retaining pad include a cellulose filter paper, glass fibers, and a nonwoven fabric. Such a labeling substance-retaining pad is prepared by impregnating the pad with a predetermined amount of the labeling substance used in detection as prepared above and then drying it.

4-7. Absorbent Pad (Water Absorbing Material)

The water absorbing material preferably has a higher ability of absorbing sample than the antibody immobilized membrane. Most preferred examples of the material is not particularly limited, and may include filter paper, absorbent paper, glass fiber cloth, glass filter, and paper such as paper towel. Other examples thereof include absorbent cotton, silica wool, glass wool, wool, silk, cotton, hemp, acrylic, rayon, nylon, nitrocellulose, cellulose acetate, regenerated cellulose, cloth or non-woven cloth composed of a fiber such as glass fiber. Also, a solid product formed with dextran, mutan, levan or cellulose powder can be used.

5. Immunological Test Method

Hereinafter, a sandwich method which is specific embodiment of the immunochromatography of the present invention, will be described. In the sandwich method, an analytical target can be analyzed by the following procedures, for example, but the procedures are not particularly limited thereto. First, a primary antibody and a secondary antibody having specificity for an analytical target (an antigen) have previously been prepared by the aforementioned method. In addition, the primary antibody has previously been labeled.

The second antibody is immobilized on a suitable insoluble thin-membrane support (e.g. a nitrocellulose membrane, a glass fiber membrane, a nylon membrane, a cellulose membrane, etc.), and it is then allowed to come into contact with a test sample (or an extract thereof) that is likely to contain the analytical target (the antigen). If the analytical target actually exists in the test sample, an antigen-antibody reaction occurs. This antigen-antibody reaction can be carried out in the same manner as that of an ordinary antigen-antibody reaction. At the same time of the antigen-antibody reaction or after completion of the reaction, an excessive amount of the labeled primary antibody is further allowed to come into contact with the resultant. If the analytical target exists in the test sample, an immune complex of the immobilized second antibody, the analytical target (antigen) and the labeled primary antibody is formed.

In the sandwich method, after completion of the reaction of the immobilized primary antibody, the analytical target (antigen) and the secondary antibody, the labeled secondary antibody that has not formed the aforementioned immune complex is removed. Subsequently, a region of the insoluble thin-membrane support, on which the second antibody has been immobilized, may be observed so as to detect or quantify the labeling substance, and detect the presence or absence of the analyte in the test sample or measure the amount of the analyte. Alternatively, a metal ion and a reducing agent are supplied, so that a signal from the labeling substance of the labeled primary antibody that has formed the aforementioned immune complex may be amplified and detected. Otherwise, a metal ion and a reducing agent are added to the labeled primary antibody, and they are simultaneously added to the thin-membrane support, so that a signal from the labeling substance of the labeled secondary antibody that has formed the aforementioned immune complex may be amplified.

6. Amplification Solution

An amplification solution that can be used in the present invention is what is called a developing solution as described in publications common in the field of photographic chemistry (e.g. "*Kaitei Shashin kagaku no kiso, Ginen shashin hen* (Revised Basic Photographic Engineering, silver salt photography)," (the Society of Photographic Science and Technology of Japan, Colona Publishing Co., Ltd.); "*Shashin no kagaku* (Photographic Chemistry)," (Akira Sasaki, Shashin Kogyo Shuppan); "*Saishin Shoho Handbook* (Latest Formulation Handbook)," (Shinichi Kikuchi et al., Amiko Shuppan); etc.).

In the present invention, any type of amplification solution can be used, as long as it is what is called a physical developing solution, which comprises silver ions, and such silver ions in the solution act as a core of development and reduction is carried out using a metal colloid as a center.

7. Compound that Contains Silver

The silver-containing compound used in the present invention may be an organic silver salt, an inorganic silver salt, or a silver complex.

The organic silver salt used in the present invention is an organic compound containing a reducible silver ion. Any one of an organic silver salt, an inorganic silver salt and a silver complex may be used as a compound containing a reducible silver ion in the present invention. For example, a silver nitrate, a silver acetate, a silver lactate, a silver butyrate, etc. have been known.

In addition, such a compound may be a silver salt or a coordination compound that forms a metallic silver relatively stable for light, when it is heated to 50° C. in the presence of a reducing agent.

The organic silver salt used in the present invention may be a compound selected from the silver salts of an azole compound and the silver salts of a mercapto compound. Such an azole compound is preferably a nitrogen-containing heterocyclic compound, and more preferably a triazole compound and a tetrazole compound. The mercapto compound is a compound having at least one mercapto group or thione group in the molecule thereof.

The silver salt of the nitrogen-containing heterocyclic compound of the present invention is preferably the silver salt of a compound having an imino group. Typical compounds include, but are not limited to, the silver salt of 1,2,4-triazole, the silver salt of benzotriazole or a derivative thereof (for example, a methylbenzotriazole silver salt and a 5-chlorobenzotriazole silver salt), a 1H-tetrazole compound such as phenylmercaptotetrazole described in U.S. Pat. No. 4,220,709, and imidazole or an imidazole derivative described in U.S. Pat. No. 4,260,677. Among these types of silver salts, a benzotriazole derivative silver salt or a mixture of two or more silver salts is particularly preferable.

The silver salt of the nitrogen-containing heterocyclic compound used in the present invention is most preferably the silver salt of a benzotrialzole derivative.

The compound having a mercapto group or a thione group of the present invention is preferably a heterocyclic compound having 5 or 6 atoms. In this case, at least one atom in the ring is a nitrogen atom, and other atoms are carbon, oxygen, or sulfur atoms. Examples of such a heterocyclic compound include triazoles, oxazoles, thiazoles, thiazolines, imidazoles, diazoles, pyridines, and triazines. However, examples are not limited thereto.

Typical examples of the silver salt of the compound having a mercapto group or a thione group include, but are not limited to, the silver salt of 3-mercapto-4-phenyl-1,2,4-triazole, the silver salt of 2-mercapto-benzimidazole, the silver salt of 2-mercapto-5-aminothiazole, the silver salt of mercaptotriazine, the silver salt of 2-mercaptobenzoxazole, and the silver salt of compounds described in U.S. Pat. No. 4,123,274.

As such a compound having a mercapto group or a thione group of the present invention, a compound that does not contain a hetero ring may also be used. As such a mercapto or thione derivative that does not contain a hetero ring, an aliphatic or aromatic hydrocarbon compound having total 10 or more carbon atoms is preferable.

Among such mercapto or thione derivatives that do no contain a hetero ring, useful compounds include, but are not limited to, the silver salt of thioglycolic acid (for example, the silver salt of S-alkylthioglycolic acid having an alkyl group containing 12 to 22 carbon atoms) and the silver salt of dithiocarboxylic acid (for example, the silver salt of dithioacetic acid and the silver salt of thioamide).

An organic compound having the silver salt of carboxylic acid is also preferably used. It is straight-chain carboxylic acid, for example. Specifically, carboxylic acid containing 6 to 22 carbon atoms is preferably used. In addition, the silver salt of aromatic carboxylic acid is also preferable. Examples of such aromatic carboxylic acid and other carboxylic acids include, but are not limited to, substituted or unsubstituted silver benzoate (for example, silver 3,5-dihydroxybenzoate, silver o-methylbenzoate, silver m-methylbenzoate, silver p-methylbenzoate, silver 2,4-dichlorobenzoate, silver acetamide benzoate and silver p-phenylbenzoate), silver tannate, silver phthalate, silver terephthalate, silver salicylate, silver phenylacetate, and silver pyromellitate.

In the present invention, aliphatic acid silver containing a thioether group as described in U.S. Pat. No. 3,330,663 can also be preferably used. A soluble silver carboxylate having a hydrocarbon chain containing an ether bond or a thioether bond, or a soluble silver carboxylate having a sterically hindered substituent on an α-position (of the hydrocarbon group) or an ortho-position (of the aromatic group) can also be used. These silver carboxylates have an improved solubility in a coating solvent, which provides a coating material having little light scattering.

Such silver carboxylates are described in U.S. Pat. No. 5,491,059. All of the mixtures of the silver salts described therein can be used in the invention, as necessary.

The silver salt of sulfonate as described in U.S. Pat. No. 4,504,575 can also be used in the embodiment of the present invention.

Further, for example, the silver salt of acetylene described in U.S. Pat. No. 4,761,361 and No. 4,775,613 can also be used in the present invention. It can be provided as a core-shell type silver salt as described in U.S. Pat. No. 6,355,408. Such silver salt is composed of a core consisting of one or more silver salts and a shell consisting of one or more different silver salts.

In the present invention, another product useful as a non-photosensitive silver source is a silver dimer composite consisting of two different types of silver salts described in U.S. Pat. No. 6,472,131. Such a non-photosensitive silver dimer composite consists of two different types of silver salts. When the aforementioned two types of silver salts include a linear saturated hydrocarbon group as a silver ligand, a difference in the numbers of carbon atoms of the ligands is 6 or greater.

The organic silver salt is contained as silver generally in an amount of 0.001 to 0.2 mol/m$^2$, and preferably 0.01 to 0.05 mol/m$^2$, in terms of the silver amount.

The inorganic silver salt or the silver complex used in the present invention is a compound containing a reducible silver ion. Preferably, such an inorganic silver salt or a silver complex is an inorganic silver salt or a silver complex, which forms metallic silver relatively stable for light, when the salt or complex is heated to 50° C. or higher in the presence of a reducing agent.

Examples of the inorganic silver salt used in the present invention include: a silver halide (such as silver chloride, silver bromide, silver chlorobromide, silver iodide, silver chloroiodide, silver chloroiodobromide, and silver iodobromide); the silver salt of a silver thiosulfate (e.g. a sodium salt, a potassium salt, an ammonium salt, etc.); the silver salt of a silver thiocyanate (e.g. a sodium salt, a potassium salt, an ammonium salt, etc.); and the silver salt of a silver sulfite (e.g. a sodium salt, a potassium salt, an ammonium salt, etc.).

The inorganic silver salt used in the present invention is preferably a silver halide or silver nitrate.

A method for forming the particles of the silver halide used in the invention is well known in the photographic industry. For example, methods described in Research Disclosure No. 17029, June 1978, and U.S. Pat. No. 3,700,458 may be used. Specifically, such a silver halide may be prepared by adding a silver-supplying compound (for example, a silver nitrate) and a halogen-supplying compound to a solution of a gelatin or other polymers.

The particle size of the silver halide is preferably very small in order to reduce examination noise. Specifically, the size is preferably 0.20 μm or less, more preferably 0.10 μm or less, and even more preferably in the range of nanoparticles. The term "particle size" is used herein to mean a diameter of a circular image having the same area as the projected area of the silver halide particle (the projected area of the main plane in the case of a tabular particle).

A silver thiosulfate, a silver thiocyanate, and a silver sulfite can also be prepared in the same manner as the formation of silver halide particles, by mixing a silver-supplying compound (such as a silver nitrate) with a thiosulfate (e.g. a sodium salt, a potassium salt, an ammonium salt, etc.), a thiocyanate (e.g. a sodium salt, a potassium salt, an ammonium salt, etc.), and a sulfite (e.g. a sodium salt, a potassium salt, an ammonium salt, etc.), respectively.

In general, if the concentration of silver ion in the amplification solution is too high, such silver ion is reduced in the amplification solution. In order to prevent such a phenomenon, a complexing agent may be used to cause the silver ion to form a complex. As such a complexing agent, amino acids such as glycine and histidine, heterocyclic bases, imidazole, benzimidazole, pyrazole, purine, pyridine, aminopyridine, nicotinamide, quinoline, and other similar aromatic heterocyclic compounds have been known. These compounds are described in E.P. Patent No. 0293947, for example. Further, as a complex salt-forming agent, thiosulfate, thiocyanate, and the like can also be used. Specific examples of the silver complex used in the present invention include a complex of a thiosulfate and a silver ion, a complex of a thiocyanate and a silver ion, a composite silver complex thereof, a complex of a sugar thione derivative and a silver ion, a complex of a cyclic imide compound (e.g. uracil, urazole, 5-methyluracil, barbituric acid, etc.) and a silver ion, and a complex of a 1,1-bissulfonylalkane and a silver ion. A preferred silver complex used in the invention is a complex of a cyclic imide compound (e.g. uracil, urazole, 5-methyluracil, barbituric acid, etc.) and a silver ion.

The silver complex used in the present invention may be prepared by a generally-known salt forming reaction. For example, the silver complex may be prepared by mixing in water or a water-miscible solvent a water-soluble silver supplier (such as a silver nitrate) with a ligand compound corresponding to the silver complex. The prepared silver complex can be used, after salts generated as by-products have been removed by a known desalting method such as dialysis or ultrafiltration.

The inorganic silver salt or the silver complex is contained as silver generally in an amount of 0.001 to 0.2 mol/m$^2$, and preferably 0.01 to 0.05 mol/m$^2$, in terms of the silver amount.

When an inorganic silver salt or a silver complex is used, a solvent for them is preferably used. The solvent used in the present invention is preferably a compound used as a ligand for forming a silver complex described in the above paragraphs for the "silver complex." Examples of such a compound used as a solvent in the present invention include a thiosulfate, a thiocyanate, a sugar thione derivative, a cyclic imide compound, and a 1,1-bissulfonylalkane. The solvent used in the present invention is more preferably a cyclic imide compound such as uracil, urazole, 5-methyluracil, or barbituric acid. The solvent used in the present invention is preferably used at a molar ratio of 0.1 to 10 moles with respect to silver ions.

8. Reducing Agent Used for Silver Ion

As a reducing agent used for silver ion, either inorganic or organic materials capable of reducing silver(I) ion to silver, or the mixtures thereof, may be used.

As an inorganic reducing agent, reducible metal salts and reducible metal complex salts whose valence can be changed with metal ions such as $Fe^{2+}$, $V^{2+}$ or $Ti^{3+}$ have been known. These salts can be used in the present invention. When such an inorganic reducing agent is used, it is necessary to form a complex with the oxidized ion or reduce it, so as to remove or detoxify the oxidized ion. For example, in a system using $Fe^{+2}$ as a reducing agent, citric acid or EDTA is used to form a complex with $Fe^{3+}$ as an oxide, so as to detoxify it.

In the present system, such an inorganic reducing agent is preferably used. The metal salt of $Fe^{2+}$ is more preferable.

Developing agents used for wet-process silver halide photographic-sensitized materials (for example, methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco dyes), or other materials known to those skilled in the art (see, for example, U.S. Pat. No. 6,020,117 (Bauer et al.)) may be used in the present invention.

The term "ascorbic acid reducing agent" means a complex of ascorbic acid and a derivative thereof. Ascorbic acid reducing agents are described in many publications, as described below, including, for example, U.S. Pat. No. 5,236,816 (Purol et al.) and publications cited therein.

The reducing agent used in the present invention is preferably an ascorbic acid reducing agent. Useful ascorbic acid reducing agents include ascorbic acid, an analogue thereof, an isomer thereof, and a derivative thereof. Examples of such compounds include the following compounds. However, examples are not limited thereto.

Examples of such compounds include D- or L-ascorbic acid and a sugar derivative thereof (for example, γ-lactoascorbic acid, glucoascorbic acid, fucoascorbic acid, glucoheptoascorbic acid, and maltoascorbic acid), sodium ascorbate, potassium ascorbate, isoascorbic acid (or L-erythroascorbic acid), and a salt thereof (for example, an alkali metal salt, an ammonium salt, or salts known in the art), and endiol-type ascorbic acid, enaminol-type ascorbic acid and thioenol-type ascorbic acid such as compounds described in U.S. Pat. No. 5,498,511, EP-A-0585,792, EP-A 0573700, EP-A 0588408, U.S. Pat. Nos. 5,089,819, 5,278,035, 5,384,232 and 5,376,510, JP 7-56286, U.S. Pat. No. 2,688,549, and Research Disclosure 37152 (March, 1995).

Among these compounds, D-, L-, and D,L-ascorbic acid (and an alkali metal salt thereof), and isoascorbic acid (and an alkali metal salt thereof) are preferable. Moreover, a sodium salt is a preferred salt thereof. If necessary, a mixture of these reducing agents may also be used.

A hindered phenol may be preferably used singly or in combination with one or more gradation-hardening reducing agents and/or contrast enhancers.

A hindered phenol is a compound having only one hydroxyl group on a benzene ring and also having at least one substituent at the ortho-position relative to the hydroxyl group. The hindered phenol reducing agent may have plural hydroxyl groups, as long as the hydroxyl groups are located on different benzene rings.

Examples of the hindered phenol reducing agent include binaphthols (that is, dihydroxybinaphthols), biphenols (that is, dihydroxybiphenols), bis(hydroxynaphthyl)methanes, bis(hydroxyphenyl)methanes (that is, bisphenols), hindered phenols, and hindered naphthols, each of which may be substituted.

Typical binaphthols include, but are not limited to, 1,1'-bi-2-naphthol, 1,1'-bi-4-methyl-2-naphthol, and compounds described in U.S. Pat. Nos. 3,094,417 and 5,262,295.

Typical biphenols include, but are not limited to, 2-(2-hydroxy-3-t-butyl-5-methylphenyl)-4-methyl-6-n-hexylphenol, 4,4'-dihydroxy-3,3',5,5'-tetra-t-butylbiphenyl, 4,4'-dihydroxy-3,3',5,5'-tetramethylbiphenyl, and compounds described in U.S. Pat. No. 5,262,295.

Typical bis(hydroxynaphthyl)methanes include, but are not limited to, 4,4'-methylenebis(2-methyl-1-naphthol) and compounds described in U.S. Pat. No. 5,262,295.

Typical bis(hydroxyphenyl)methanes include, but are not limited to, bis(2-hydroxy-3-t-butyl-5-methylphenyl)methane (CAO-5), 1,1'-bis(2-hydroxy-3,5-dimethylphenyl)-3,5,5-trimethyl hexane (NONOX or PERMANAX WSO), 1,1'-bis(3,5-di-t-butyl-4-hydroxyphenyl)methane, 2,2'-bis(4-hydroxy-3-methylphenyl)propane, 4,4'-ethylidene-bis(2-t-butyl-6-methylphenol), 2,2'-isobutylidene-bis(4,6-dimethylphenol) (LOWINOX 221B46), 2,2'-bis(3,5-dimethyl-4-hydroxyphenyl)propane, and compounds described in U.S. Pat. No. 5,262,295.

Typical hindered phenols include, but are not limited to, 2,6-di-t-butylphenol, 2,6-di-t-butyl-4-methylphenol, 2,4-di-t-butylphenol, 2,6-dichlorophenol, 2,6-dimethylphenol, and 2-t-butyl-6-methylphenol.

Typical hindered naphthols include, but are not limited to, 1-naphthol, 4-methyl-1-naphthol, 4-methoxy-1-naphthol, 4-chloro-1-naphthol, 2-methyl-1-naphthol, and compounds described in U.S. Pat. No. 5,262,295.

Moreover, other compounds disclosed as reducing agents include amidoximes (for example, phenylamidoxime), 2-thienylamidoxime, p-phenoxyphenylamidoxime, a combination of an aliphatic carboxylic allyl hydrazide and ascorbic acid (for example, a combination of 2,2'-bis(hydroxymethyl)-propionyl-β-phenyl hydrazide and ascorbic acid), a combination of a polyhydroxybenzene and at least one of hydroxylamine, reductone and hydrazine (for example, a combination of hydroquinone and bis(ethoxyethyl)hydroxylamine), piperidi-4-methylphenylhydrazine, hydroxamic acids (for example, phenylhydroxamic acid, p-hydroxyphenylhydroxamic acid, and o-alaninehydroxamic acid), a combination of an azine and a sulfonamidophenol (for example, a combination of phenothiazine and 2,6-dichloro-4-benzenesulfonamidophenol), α-cyanophenylacetic acid derivatives (for example, ethyl-α-cyano-2-methylphenylacetic acid and ethyl-α-cyanophenylacetic acid), bis-o-naphthol (for example, 2,2'-dihydroxy-1-binaphthyl, 6,6'-dibromo-2,2'-dihydroxy-1,1'-binaphthyl, and bis(2-hydroxy-1-naphthyl)methane), a combination of bis-naphthol and a 1,3-dihydroxybenzene derivative (for example, 2,4-dihydroxybenzophenone and 2,4-dihydroxyacetophenone), 5-pyrazolones (for example, 3-methyl-1-phenyl-5-pyrazolone), reductones (for example, dimethylaminohexose reductone, anhydrodihydro-aminohexose reductone, and anhydrodihydro-piperidone-hexose reductone), indane-1,3-diones (for example, 2-phenylindane-1,3-dione), chromans (for example, 2,2-dimethyl-7-t-butyl-6-hydroxychroman), 1,4-dihydroxypyridines (for example, 2,6-dimethoxy-3,5-dicarbetoxy-1,4-dihydropyridine), ascorbic acid derivatives (1-ascorbic palmitate, ascorbic stearate), unsaturated aldehydes (ketones), and 3-pyrazolidones.

Examples of a reducing agent that can be used in the present invention include substituted hydrazines such as sulfonyl hydrazines described in U.S. Pat. No. 5,464,738. Other useful reducing agents are described, for example, in U.S. Pat. Nos. 3,074,809, 3,094,417, 3,080,254 and 3,887,417. Auxiliary reducing agents desried in U.S. Pat. No. 5,981,151 are also useful.

The reducing agent may be a combination of a hindered phenol reducing agent and a compound selected from various auxiliary reducing agents such as those mentioned below. In addition, a mixture of such a combined agent plus a contrast enhancer (that is, a mixture of the 3 components) is also useful. As such an auxiliary reducing agent, it is possible to use trityl hydrazide and formyl-phenyl hydrazide described in U.S. Pat. No. 5,496,695.

A contrast enhancer may be used in combination with the reducing agent. Useful contrast enhancers include, but are not limited to, hydroxylamines (including hydroxylamine and alkyl- and aryl-substituted derivatives thereof), alkanolamines and phthalic ammonium described in U.S. Pat. No. 5,545,505, hydroxamic acid compounds described in U.S. Pat. No. 5,545,507, N-acylhydrazine compounds described in U.S. Pat. No. 5,558,983, and hydrogen atom donor compounds described in U.S. Pat. No. 5,637,449.

Not all combinations of reducing agents and organic silver salts are equally effective. A preferred combination is a benzotriazole silver salt used as an organic silver salt, a substituted compound thereof or a mixture thereof, with an ascorbic acid reducing agent used as a reducing agent.

The reducing agent of the present invention may be contained in an amount of 1 mass % to 10 mass % (dry mass) based on the amount of silver in organic silver. When the reducing agent is added to a layer other than the layer containing the organic silver salt in a multilayer structure, the amount of the reducing agent is slightly higher, and it is desirably from approximately 2 mass % to approximately 15 mass %. An auxiliary reducing agent is contained in an amount of about 0.001 mass % to 1.5 mass % (dry weight).

9. Other Auxiliary Agents

Other auxiliary agents contained in the amplification solution may include a buffer, an antiseptic such as an antioxidant or an organic stabilizer, and a speed regulator. Examples of a buffer used herein include buffers comprising acetic acid, citric acid, sodium hydroxide, a salt thereof, or tris(hydroxymethyl)aminomethane, and other buffers used in ordinary chemical experiments. Using these buffers as appropriate, the pH of the amplification solution can be adjusted to the optimal pH.

The present invention will be more specifically described in the following examples. However, these examples are not intended to limit the scope of the present invention.

EXAMPLES

In Examples, it was demonstrated below that the immunochromatographic kit of the present invention is highly sensitive in an hCG detection system.

(1) Preparation of Anti-hCG Antibody-Labeled Gold Colloid (Diameter: 50 mm) the Labeling Product for Detection)

1 mL of 50 µg/mL anti-hCG monoclonal antibody (Anti-hCG 5008 SP-5, Medix Biochemica) solution was added to a gold colloidal solution having pH adjusted by addition of 1 mL of a 50 mM $KH_2PO_4$ buffer (pH 7.0) to 9 mL of a 50-nm diameter gold colloidal solution (EM.GC50, BBI), followed by stirring. The mixture was allowed to stand for 10 minutes and then 550 µL of 4 mM HS-PEG (mercaptopolyethylene glycol (Mw. 10000, Product name SUNBRIGHT ME-100SH, NOF Corporation) aqueous solution was added to the solution, followed by stirring. The solution was allowed to stand for 5 minutes. Subsequently, 550 µL of 4 mM HS-PEG (mercaptopolyethylene glycol (Mw. 2000, Product name SUNBRIGHT ME-020SH, NOF Corporation) aqueous solution was added to the solution, followed by stirring. The solution was allowed to stand for 5 minutes. The solution was centrifuged (himac CF16RX, Hitachi) at 8000×g and 4° C. The supernatant was removed so that approximately 1 mL of the solution remained. The gold colloid was dispersed again using an ultrasonic washing machine. The time for centrifugation was 15 minutes. Subsequently, the resultant was then dispersed in 20 mL of a gold colloidal stock solution (20 mM Tris-HCl buffer (pH 8.2), 0.05% PEG (Mw. 20000), 150 mM NaCl, 1% BSA, and 0.1% $NaN_3$) and then centrifuged again at 8000×g and 4° C. for 15 minutes. The supernatant was removed so that approximately 1 mL of the solution remained. The gold colloid was dispersed again using an ultrasonic washing machine, so that an antibody-labeled gold colloidal (50 nm) solution was obtained.

(2) Preparation of Gold Colloidal Antibody Holding Pad

Each antibody-labeled gold colloid prepared in (1) above was diluted with water and a coating solution for a gold colloid (20 mM Tris-Hcl buffer (pH 8.2), 0.05% PEG (Mw: 20000), and 5% sucrose) to set the OD at 520 nm to 1.5. This solution was uniformly applied to glass fiber pads (Glass Fiber Conjugate Pad, Millipore Corporation) cut to the size of 8 mm×150 mm in an amount of 0.8 mL per pad. The pads were dried under reduced pressure overnight to obtain gold colloidal antibody holding pads.

(3) Preparation of Antibody-Immobilized Membrane (Chromatographic Carrier)

An antibody-immobilized membrane was prepared in the following manner by immobilizing an antibody on a nitrocellulose membrane (HiFlow Plus HF120 with a plastic lining, Millipore Corporation) cut to the size of 25 mm×200 mm. The membrane, with one of its long sides facing downward, was coated with an anti-hCG monoclonal antibody (for immobilization) (Anti-Alpha subunit 6601 SPR-5, Medix Biochemica) solution prepared to a concentration of 0.5 mg/ml with the use of a coater of inkjet type (BioDot Ltd.). Specifically, the membrane was coated so that a linear portion thereof 8 mm above the lower edge was coated to have a width of approximately 1 mm (so as to form a "detection part(s)"). In a similar manner, the membrane was coated with a control anti-mouse IgG antibody (anti-mouse IgG (H+L), rabbit F(ab')2, Product No. 566-70621, Wako Pure Chemical Industries, Ltd.) solution prepared to a concentration of 0.5 mg/ml, so that a linear portion thereof 12 mm above the lower edge was coated (so as to form a "control part(s)"). The coated membrane was dried at 50° C. for 30 minutes with a hot-air dryer. The membrane was immersed in 500 ml of a blocking solution (50 mM borate buffer (pH 8.5) containing 0.5% by weight casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (0.5% by weight sucrose, 0.05% by weight sodium cholate, and 50 mM Tris-HCl (pH 7.5)) in a similar vat and then allowed to stand therein for 30 minutes. The membrane was removed from the solution and then dried overnight at room temperature to obtain an antibody-immobilized membrane.

(4) Preparation of Immunochromatographic Kit

The antibody-immobilized membrane prepared in (3) was adhered to a back pressure-sensitive adhesive sheet 1 (ARcare9020, NIPPN TechnoCluster, Inc.). At this time, the membrane was used with the anti-hCG antibody line side (one of the long sides of the membrane) facing downward. The gold colloidal antibody holding pad 2 prepared in 2 was adhered onto the antibody-immobilized membrane such that the pad 2 overlapped the lower portion of the antibody-immobilized membrane by approximately 2 mm. The sample addition pad 5 (glass fiber pad (Glass Fiber Conjugate Pad, Millipore Corporation) cut to the size of 18 mm×150 mm was adhered to the gold colloidal antibody holding pad 2 such that the sample addition pad 5 overlapped the lower portion of the gold colloidal antibody holding pad by approximately 4 mm. Furthermore, absorbent pad 4 (cellulose membrane cut to the size of 20 mm×5 mm (Comparative example) (Cellulose Fiber Sample Pad, Millipore Corporation)) was adhered onto the antibody-immobilized membrane such that the absorbent pad 4 overlapped the upper portion of the antibody-immobilized membrane by approximately 5 mm. With the use of a guillotine cutter (CM4000, NIPPN TechnoCluster, Inc.), the thus overlapped and adhered members were cut in parallel to the short sides of the overlapped members at 5-mm intervals, whereby 5 mm×55 mm immunochromatographic strips having a width of 5 mm were prepared. These strips were placed in a plastic case (NIPPN TechnoCluster, Inc.), so as to prepare an immunochromatographic kit for testing.

(5) Evaluation of Sensitivity by Silver Salt Amplification hCG (recombinant hCG R-506, ROHTO Pharmaceutical Co., Ltd.) was dissolved in PBS buffer containing 1% by weight BSA, so that hCG solutions for testing having different concentrations were prepared.

The hCG solutions (100 µL each) having different concentrations were each applied dropwise to each immunochromatographic kit for testing. The kit was allowed to stand for 10 minutes. Each membrane was removed from a case and then placed in a microtube (BM Equipment Co., Ltd, BM4020) containing 700 µL of PBS buffer containing 1% by weight BSA, so that the portions to which the sample had been applied dropwise were immersed in the solution. The membrane under such conditions was then washed for 1 hour.

The membrane was then placed in a microtube (BM Equipment Co., Ltd, BM4020) containing 200 µL of the following amplification solution A, so that the portions to which the sample had been applied dropwise were immersed in the solution. The time point at which the membrane absorbed the amplification solution so that the amplification solution reached the detection line was determined to be 0 minutes. At 30 seconds after the time point (0 minutes), the membrane was removed and then immediately washed with water for 3 minutes. The degrees of color development confirmed when the detection lines were visually observed were determined on a scale of one to five, dark color development "C," presence of color development "D," light color development "E," slight color development "E-," and no color development "0."

Composition and Preparation Method for Silver Amplification Solution A

1) Preparation of Amplification Solution A-1

Forty (40) mL of 1 mol/L iron nitrate aqueous solution (prepared by dissolving iron (III) nitrate nonahydrate (Product No. 095-00995, Wako Pure Chemical Industries, Ltd.) in water), 10.5 g of citric acid (Product No. 038-06925, Wako Pure Chemical Industries, Ltd.), 0.1 g of dodecylamine (Product No. 123-00246, Wako Pure Chemical Industries, Ltd.), and 0.44 g of surfactant $C_9H_{19}$—$C_6H_4$—O—$(CH_2CH_2O)_{50}$H were dissolved in 325 g of water. After they were all dissolved, 40 mL of nitric acid (10%) was added to the solution while stirring it using a stirrer. Eighty (80) mL of the solution was weighed and then 11.76 g of iron (II) ammonium sulfate hexahydrate (Product No. 091-00855, Wako Pure Chemical Industries, Ltd.) was added to the solution. The thus obtained solution was designated amplification solution A-1.

2) Preparation of Amplification Solution A-2

Water was added to 10 mL of a silver nitrate solution (containing 10 g of silver nitrate) to a total amount of 100 g. Amplification solution A-2 (10% by weight silver nitrate aqueous solution) was thus prepared.

3) Preparation of Amplification Solution A

Forty (40) mL of amplification solution A-1 was weighed and then 4.25 mL of amplification solution A-2 was added to the solution, followed by stirring, thereby preparing amplification solution A.

Example 1

The sensitivity of an immunochromatographic kit (a gold colloid was treated with a blocking agent (a mixture of HS-PEG (16.7%) having a molecular weight of 2000 and HS-PEG (83.3%) having a molecular weight of 10000)) prepared by the above method was evaluated by an argentate amplification method.

Comparative Example 1

The sensitivity of an immunochromatographic kit (a gold colloid was treated with a blocking agent according to a conventional method (1% polyethylene glycol (PEG Mw. 20000, Product No. 168-11285, Wako Pure Chemical Industries, Ltd.) and 10% bovine serum albumin (BSA FractionV, Product No. A-7906, SIGMA)) prepared by the above method was evaluated by an argentate amplification method.

Comparative Example 2

The sensitivity of an immunochromatographic kit (a gold colloid was treated with a blocking agent (HS-PEG with a molecular weight of 20000)) prepared by the above method was evaluated by an argentate amplification method.
Result:

As shown in the results in Table 1, Example 1 and Comparative example 1 revealed that the use of a mixture of HS-PEGs differing in molecular weight could significantly increased the sensitivity compared with the conventional method when labeled fine gold particles were blocked after coating with an antibody. Moreover, Comparative example 2 revealed that the use of only one type of HS-PEG exerted no effect of increasing the sensitivity.

TABLE 1

| Antigen concentration (M) | Comparative example 1 | Comparative example 2 | Example 1 |
|---|---|---|---|
| 1.1E−12 | C | E | C |
| 5.6E−13 | D | 0 | D− |
| 2.8E−13 | E | 0 | D |
| 1.4E−13 | E− | 0 | D |
| 7.0E−14 | E− | 0 | D |
| 0 | 0 | 0 | 0 |

Next, the following immunochromatographic kits were prepared using F(ab')₂ anti-influenza antibodies as fragmented antibodies, so that the effects of the present invention were demonstrated.

(6) Preparation of F(ab')₂ Anti-Influenza A Virus Antibody

An anti-influenza A virus antibody (Product No. 7307, Medix Biochemica) was prepared using an ImmunoPure® IgG1 Fab and F(ab')₂ Preparation Kit (Product No. 44880, Pierce).

(7) Preparation of F(ab')₂ Anti-Influenza B Virus Antibody

An anti-influenza B virus antibody (Product No. 1131 (ViroStat, Inc.)) and lysyl endopeptidase (Product No. 125-05061, Wako Pure Chemical Industries, Ltd.) were diluted with a 50 mM Tris-HCL buffer (pH 8.5) at a molar ratio of 1:100, followed by 3 hours of reaction at 37° C. Subsequently, the F(ab')$_2$ antibody was purified using an ImmunoPure (A) IgG Purification Kit (Product No. 44667, Pierce).

(8) Preparation of Kit Using F(ab')$_2$ Anti-Influenza Virus Antibody-Labeled Gold Colloid Regarding preparation of antibody-labeled gold colloidal solutions, the following similar procedures were carried out separately for the A antibody and the B antibody prepared in (6) and (7).

1 mL of a 150 μg/mL F(ab')$_2$ antibody solution was added to a gold colloidal solution having pH adjusted by addition of 1 mL of a 20 mM Borax buffer (pH 8.5) to 9 mL of a 50-nm diameter gold colloidal solution (EM.GC50, BBI), followed by stirring. The solution was allowed to stand for 10 minutes, a blocking agent A was added to the solution, and then the solution was allowed to stand for 5 minutes. Next, a blocking agent B was added, and then the solution was allowed to stand for 5 minutes. The solution was centrifuged at 8000×g and 4° C. for 30 minutes (himacCF16RX, Hitachi). The supernatant was removed so that approximately 1 mL of the solution remained. The gold colloid was dispersed again using an ultrasonic washing machine. Subsequently, the resultant was then dispersed in 20 mL of a gold colloidal stock solution (20 mM Tris-HCl buffer (pH 8.2), 0.05% PEG (Mw.20000), 150 mM NaCl, 1% BSA, and 0.1% NaN$_3$) and then centrifuged again at 8000×g and 4° C. for 30 minutes. The supernatant was removed so that approximately 1 mL of the solution remained. The gold colloid was dispersed again using an ultrasonic washing machine, so that an antibody-labeled gold colloidal (50 nm) solution was obtained.

(9) Preparation of Gold Colloidal Antibody Holding Pad

Each antibody-labeled gold colloid prepared described above was diluted with water and a coating solution for a gold colloid (20 mM Tris-Hcl buffer (pH 8.2), 0.05% PEG (Mw: 20000), and 5% sucrose) to set the OD at 520 nm to 3.0. These solutions were mixed at a ratio of 1:1 and then uniformly applied to glass fiber pads cut to the size of 8 mm×150 mm in an amount of 0.8 mL per pad. The pads were dried under reduced pressure overnight to obtain gold colloidal antibody holding pads.

(10) Preparation of Anti-Influenza Antibody-Immobilized Membrane (Chromatographic Carrier)

An antibody-immobilized membrane was prepared in the following manner by immobilizing antibodies on nitrocellulose membranes (HiFlow Plus HF120 with a plastic lining, Millipore Corporation) cut to the size of 25 mm×200 mm. A membrane, with one of its long sides facing downward, was coated with an anti-influenza A virus antibody solution prepared to a concentration of 1.5 mg/ml with the use of a coater of inkjet type, so that a linear portion thereof 7 mm above the lower edge was coated to have a width of approximately 1 mm. In a similar manner, a membrane was coated with an anti-influenza B virus antibody solution prepared to a concentration of 1.5 mg/ml with the use of a coater of inkjet type, so that a linear portion thereof 10 mm above the lower edge was coated to have a width of approximately 1 mm. Furthermore, a membrane was coated with a control anti-mouse IgG antibody solution prepared to a concentration of 0.5 mg/mL, so that a linear portion thereof 13 mm above the lower edge was coated. Each coated membrane was dried at 50° C. for 30 minutes with a hot-air dryer. The membrane was immersed in 500 ml of a blocking solution (50 mM borate buffer (pH 8.5) containing 0.5 w % casein (milk-derived product, Product No. 030-01505, Wako Pure Chemical Industries, Ltd.)) in a vat and then allowed to stand therein for 30 minutes. Thereafter, the membrane was transferred to and immersed in 500 ml of a washing-stabilizing solution (0.5 w % sucrose, 0.05 w % sodium cholate, and 50 mM Tris-HCl (pH 7.5)) in a similar vat and then allowed to stand therein for 30 minutes. The membrane was removed from the solution and then dried overnight at room temperature to give an antibody-immobilized membrane.

(11) Assembly of Kit

The antibody-immobilized membrane prepared in 3 was adhered to a back pressure-sensitive adhesive sheet (AR-care9020, NIPPN TechnoCluster, Inc.). At this time, a membrane was used with the anti-influenza A antibody line side (one of the long sides of the membrane) facing downward. The gold colloidal antibody holding pad prepared in 2 was adhered onto the antibody-immobilized membrane such that the pad overlapped the lower portion of the antibody-immobilized membrane by approximately 2 mm. A sample addition pad (glass fiber pad (Glass Fiber Conjugate Pad, Millipore Corporation) cut to the size of 18 mm×150 mm) was adhered to the gold colloidal antibody holding pad such that the sample addition pad overlapped the lower portion of the gold colloidal antibody holding pad by approximately 4 mm. Furthermore, an absorbent pad (cellulose membrane cut to the size of 5 mm×100 mm (Cellulose Fiber Sample Pad, Millipore Corporation)) was adhered onto the antibody-immobilized membrane such that the absorbent pad overlapped the upper portion of the antibody-immobilized membrane by approximately 5 mm. With the use of a guillotine cutter (CM4000, NIPPN TechnoCluster, Inc.), the thus overlapped and adhered members were cut in parallel to the short sides of the overlapped and adhered members at 5-mm intervals, whereby immunochromatographic strips having a width of 5 mm were prepared. These strips were placed in a plastic case (NIPPN TechnoCluster, Inc.), so as to prepare an immunochromatographic kit for testing.

Comparative Example 3

In the method for producing an influenza immunochromatographic kit, blocking agent A was 550 μL of 1% polyethylene glycol (PEG Mw.20000, Product No. 168-11285, Wako Pure Chemical Industries, Ltd.) aqueous solution and blocking agent B was 1.1 mL of 10% bovine serum albumin (BSA FractionV, Product No. A-7906, SIGMA) aqueous solution.

Comparative Example 4

In the method for producing an influenza immunochromatographic kit, blocking agent A was 1.1 mL of 4 mM HS-PEG (mercaptopolyethylene glycol (Mw. 20000, Product name: SUNBRIGHT ME-200SH, NOF Corporation)) aqueous solution, and no agent was added as blocking agent B.

Example 2

In the method for producing an influenza immunochromatographic kit, blocking agent A was 550 μL of 4 mM HS-PEG (mercaptopolyethylene glycol (Mw. 10000, Product name: SUNBRIGHT ME-100SH, NOF Corporation)) aqueous solution and blocking agent B was 550 μL of 4 mM HS-PEG (mercaptopolyethylene glycol (Mw.2000, Product name: SUNBRIGHT ME-020SH, NOF Corporation)) aqueous solution.

(12) Evaluation of Sensitivity by Silver Salt Amplification

The sensitivity of each prepared immunochromatographic kit was evaluated by the same method as that of (5) Evaluation of sensitivity by argentate amplification in the hCG system except that the positive control of Quick S-Influ A•B "Seiken" negative/positive controls (Product No. 322968, DENKA SEIKEN Co., Ltd.) was used as an antigen instead of hCG for PBS buffer containing 1% by weight BSA. The antigen solution used herein contained both the antigen for influenza A virus and the antigen for influenza B virus. Thus, when these antigens were present, both A virus and B virus could be detected at the same time.

Result:

As a result for Example 2 and Comparative example 3 shown in Table 2, also in the case of using fragmented antibodies, when labeled gold fine particles coated with the antibodies were blocked, HS-PEGs differing in molecular weight were mixed and used, so that the resulting sensitivity was increased compared with the conventional method (Comparative example 3). The effects of the present invention could thus be confirmed. In addition, it was confirmed in Comparative example 4 that the effect of increasing the sensitivity was not exerted in a case in which only one type of HS-PEG was used.

TABLE 2

| Positive control dilution ratio Detected | Comparative example 3 | | Comparative example 4 | | Example 2 | |
|---|---|---|---|---|---|---|
| virus | Type A | Type B | Type A | Type B | Type A | Type B |
| 1/640 | E− | E | E− | E− | D | D |
| 1/1280 | E− | E− | 0 | 0 | E | E |
| 1/2560 | 0 | 0 | 0 | 0 | E− | E |
| 1/5120 | 0 | 0 | 0 | 0 | E− | E− |
| 1/10240 | 0 | 0 | 0 | 0 | 0 | 0 |
| 0 | 0 | 0 | 0 | 0 | 0 | 0 |

The invention claimed is:

1. A metal particle, which is produced by coating a metal particle labeled with a molecule binding to an analyte with a mixture of two or more types of water-soluble polymers having a mercapto group, a dithiol group or a sulfide group and differing in molecular weight, wherein the water-soluble polymers include:
   (A) a polyalkylene oxide polymer that has a mercapto group, a dithiol group or a sulfide group and that has a molecular weight of 5,000 to 100,000; and
   (B) a polyalkylene oxide polymer that has a mercapto group, a dithiol group or a sulfide group and that has a molecular weight of 1,000 to 5,000.

2. The metal particle according to claim 1, wherein each content of the two or more types of water-soluble polymer ranges from 0.001% by weight to 99.999% by weight.

3. The metal particle according to claim 1, wherein the water-soluble polymers are polyalkylene oxide polymers having a mercapto group, a dithiol group or a sulfide group.

4. The metal particle according to claim 1, wherein the water-soluble polymers are polyethylene glycols having a mercapto group, a dithiol group or a sulfide group.

5. The metal particle according to claim 1, wherein the metal particle is a gold colloidal particle.

6. An immunochromatographic kit, which comprises at least (a) the metal particle of claim 1, (b) a reagent for a sensitization reaction, and (c) a porous carrier.

7. A testing method, which comprises developing a complex formed of an analyte and the metal particle of claim 1 on an insoluble carrier and capturing the complex of the analyte and the metal particle at a reaction site on the insoluble carrier that has a second molecule binding to the analyte, so as to detect the analyte.

8. The testing method according to claim 7, wherein amplification is carried out using silver or a silver compound.

9. The metal particle according to claim 1, wherein the molecule binding to an analyte is an antibody.

10. The metal particle according to claim 1, wherein polymers (A) and (B) are polyalkylene oxide polymers having a mercapto group.

11. The metal particle according to claim 1, wherein polymers (A) and (B) are mercaptopolyethylene glycols.

* * * * *